United States Patent [19]

Soane et al.

[11] Patent Number: 5,126,022

[45] Date of Patent: Jun. 30, 1992

[54] METHOD AND DEVICE FOR MOVING MOLECULES BY THE APPLICATION OF A PLURALIT OF ELECTRICAL FIELDS

[75] Inventors: David S. Soane; Zoya M. Soane, both of Piedmont, Calif.

[73] Assignee: Soane Tecnologies, Inc., Hayward, Calif.

[21] Appl. No.: 487,021

[22] Filed: Feb. 28, 1990

[51] Int. Cl.⁵ .............................................. G01N 27/26
[52] U.S. Cl. ............................. 204/180.1; 204/182.8; 204/183.1; 204/299 R; 204/300 R
[58] Field of Search ............. 204/182.8, 299 R, 183.1, 204/300 R, 180.1

[56] References Cited

U.S. PATENT DOCUMENTS

| | | | |
|---|---|---|---|
| 4,471,647 | 9/1984 | Jerman et al. | 73/23 |
| 4,474,889 | 10/1984 | Terry et al. | 436/161 |
| 4,740,283 | 4/1988 | Laas et al. | 204/183.1 |
| 4,834,862 | 5/1989 | Breiner et al. | 204/301 |
| 4,891,120 | 6/1990 | Sethi et al. | 204/299 R |
| 4,908,112 | 3/1990 | Pace | 204/299 R |
| 4,911,817 | 3/1990 | Kindlmann | 204/182.8 |
| 4,935,040 | 6/1990 | Goedert | 210/198.3 |

FOREIGN PATENT DOCUMENTS

| | | |
|---|---|---|
| 0361046 | 8/1989 | European Pat. Off. |
| 0356187 | 2/1990 | European Pat. Off. |
| WO84/02001 | 5/1984 | PCT Int'l Appl. |

Primary Examiner—John Niebling
Assistant Examiner—David G. Ryser
Attorney, Agent, or Firm—Kilpatrick & Cody

[57] ABSTRACT

Devices and methods are disclosed for moving charged molecules through a medium by the application of a plurality of electrical fields of sufficient strength and applied for sufficient amounts of time so as to move the charged molecules through the medium. The devices although preferably small in size, preferably generate large numbers (100 or more) of electrical fields to a movement area which preferably contains a liquid buffered or gel medium. Mixtures of charged molecules are pulled through the gel by the force of the electrical fields. The fields are preferably activated simultaneously or sequentially one after another at various speeds to create complex force field distributions or moving field waves along the separation medium. Charged molecules capable of moving quickly through the gel will be moved along by the faster moving field waves and be separated from slower moving molecules. The fields can be activated by computer software and can be used to move molecules away from and toward each other to obtain rapid and complex chemical synthesis, sequencing or reaction protocols.

21 Claims, 1 Drawing Sheet

METHOD AND DEVICE FOR MOVING MOLECULES BY THE APPLICATION OF A PLURALIT OF ELECTRICAL FIELDS

FIELD OF THE INVENTION

This invention relates generally to the fields of electrophoresis and photolithography which is applied in a manner so as to integrate technological innovations in the fields of biochemistry, polymer science, molecular genetics and electronics. More specifically, the invention relates to a method of moving charged molecules or particles in a medium by the simultaneous or sequential application of a plurality of electrical fields and devices for carrying out that method.

BACKGROUND OF THE INVENTION

Electrophoresis is an analytical technique to separate and identify charged particles, ions, or molecules. It involves the imposition of an electric field to move charged species in a liquid medium. The most often studied species are bio-macromolecules, such as proteins and DNA fragments, which are usually polyelectrolytes. However, electrophoresis can be used to separate any charged materials including various cells, bacteria and viral materials. At a fixed pH and ionic strength, a given polyelectrolyte acquires a certain number of net charges. Such particles are surrounded by counter-ions and have various charges, sizes (volume and shape) which effect movement. Molecules are separated by their different mobilities under an applied electric field. The mobility variation derives from the different charge and frictional resistance characteristics of the molecules. The more charged and streamlined the molecules, the faster their movement.

When a mixture containing several molecular species is introduced into an electrophoretic separation medium and an electric field is applied, the different charged components migrate at various speeds in the system leading to the resolution of the mixture. Bands appear, depending on the mobilities of the components. The exact location (thus time of emergence of the components at the end of the medium opposite to the point of introduction) depends on the interaction of the polyelectrolytes with the surrounding medium, via the influence of pH, ionic strength, ion type and whether the medium is a buffered solution of ions, polymeric solution, or gel such as a cross-linked gel. Cross-linked gels and polymeric solutions can affect separation by size or sieving. Hence, electrophoresis can be classified into two basic types including (1) free solution and (2) gel electrophoresis. The most frequently used gel media are based on polyacrylamide (known as PAGE) and agarose gels.

The combination of free solution and gel electrophoretic separation experiments gives a plethora of information, such as the number and relative amounts of the components in a mixture. When the components are specifically identified, e.g., by antigen-antibody binding, unequivocal identification of the presence of the given component is afforded. As a consequence, electrophoresis has become the cornerstone of macromolecular analysis in biotechnology.

Traditional electrophoretic media are large in dimension, being on the order of mm. A recent development in the field of electrophoretic technology is high performance capillary electrophoresis. In accordance with this methodology the separation media are made of hollow fibers with an inner diameter of 25 to 100 microns. This separation configuration allow a high current to pass through the media in the hollow fiber. The Joule heating can be efficiently removed due to the small size of the capillary. As a result, sample analysis time is greatly reduced. However, such high performance electrophoresis still requires the use of a high voltage DC power supply (e.g., up to tens of kv) to accomplish separation. In addition, gel-filled capillaries are not commercially available and are difficult to make. The parallel idea in slab gel media involves the use of very thin slabs. Here, gel formation involves sufficient shrinkage, making the edges of the slab more stressed than the center. Hence, if the same sample is separated using both an edge and a center track, it will exhibit different resolved patterns. This is a major problem in slab gel electrophoresis. Here again, as in capillary electrophoresis, high voltage power supplies are needed and the resulting resolution (although the best available) is not entirely satisfactory.

In both capillary and slab electrophoresis, the field applied is fixed, thus passive. Although crossed field and pulsed field electrophoresis (2D electrophoresis) methods have been described, their application is limited. In all cases, the entire separation media, free solution or gel, are under the same applied field at a given time. The field may change temporally, but not spatially by design. Accordingly, the entire sample of charged particles to be separated are under the same field at any given time.

SUMMARY OF THE INVENTION

The present invention relates to moving charged particles such as charged molecules within a medium in response to a plurality of electrical fields which are continuously applied simultaneously and/or sequentially along the medium containing the charged molecules in order to move the charged molecules in a precise and controlled fashion. The movement of the electrical fields can be accurately controlled both spatially and temporally. Charged particles in the medium can be moved so as to separate particular types of charged particles away from one another and thus provide a highly defined analytical technique. Further, specific charged molecules can be moved towards each other into precisely defined regions in order to react particular types of molecules together in a synthesis or sequencing protocol.

In accordance with one aspect of the invention, there is provided a charged particles moving device such as an electrophoresis device produced by any of a variety of procedures such as photolithography silk-screening, LASER technologies, or vapor deposition which results in a patterning of electrical circuitry. In accordance with this device, there is provided a "movement area" which includes a medium in which the charged particles such as charged molecules are to be moved. The movement area is positioned so that it can be continuously subjected to a plurality of electrical fields in a simultaneous or sequential manner. The electrical fields effecting the movement area are activated so as to move charged molecules in a controlled manner through the medium in the movement area. Accordingly, mixtures of different types of charged molecules can be separated away from each other in order to provide an analytical technique.

As a device for conducting reactions (e.g., sequencing synthesis methods), the different fields connected to the movement area can be applied so as to move specific types of charged molecules into contact with other types of charged molecules in order to react the molecules and carry out any number of different reaction protocols. The electrical connections contacting the movement area are preferably in the form of intelligent integrated circuitry which is interactive with a computer system capable of activating the fields in any given manner so as to create precise types of separation of molecules for analysis or combinations of molecules for reaction.

A primary object of the present invention is to provide a device which is capable of moving charged particles through a medium in a precise controlled fashion in response to a plurality of different electrical fields, which fields are preferably generating forces which vary in time and space simultaneously.

Another object of the present invention is to provide a device which separates mixtures of charged particles such as charged molecules within a medium by the application of a plurality of electrical fields to the medium in a simultaneous and/or sequential fashion.

A feature of the present invention is that a plurality (preferably large numbers) of different electrical fields are applied to a medium in order to move molecules within the medium in a precise manner.

An advantage of the present invention is that molecules can be moved within a given medium so as to provide finer separations of molecules than is possible with conventional separation techniques.

Yet another advantage of the present invention is that devices of the invention can be efficiently and economically produced.

Yet another advantage of the present invention is the minimization or elimination of electroendosmosis by the utilization of polymeric substrates, such as polymethylmethacrylate.

Another feature of the devices of the present invention is the use of movement areas which have a cross-sectional shape which includes flattened or slab-like regions which regions allow for the efficient accurate use of spectrometer devices which can be used in connection with the invention.

Yet another feature of the invention is the inclusion of branched movement areas in which it is possible to move together and separate from each other charged particles in order to carry out complex reaction and/or separate schemes.

Yet another advantage of the present invention is the use of inert polymeric substrate materials on components which might contact charged particles to be separated or combined which materials minimize protein absorption and loss of sample materials being separated and/or combined.

Still another advantage of the present invention is that it makes possible the use of substantially smaller voltages due to the small spacing of the electrodes thus providing for a safer device for laboratory use as well as conserving power.

These and other objects, advantages and features of the present invention will become apparent to those persons skilled in the art upon reading the details of the structure of the devices and methods of operation as more fully set forth below, reference being made to the accompanying drawings forming a part hereof.

DETAILED DESCRIPTION OF THE INVENTION

Figure 1:
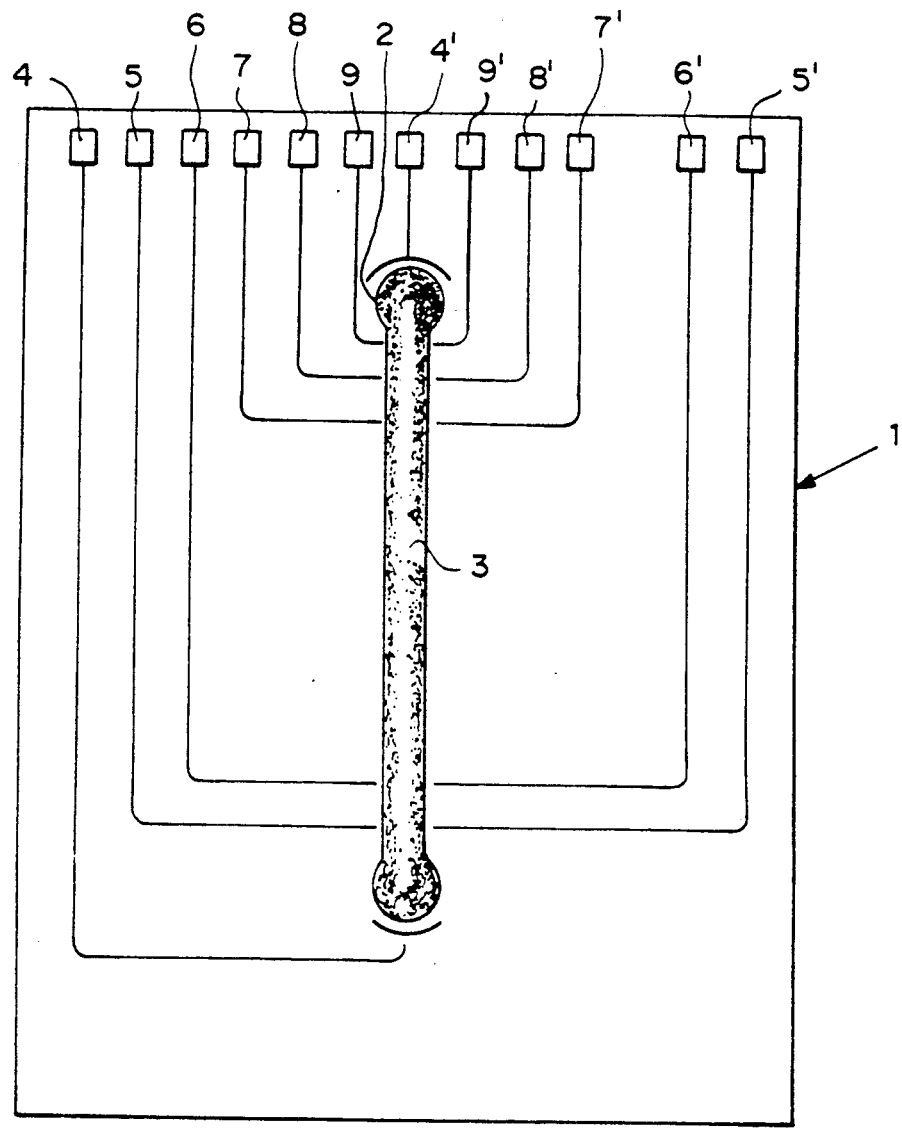
FIG. 1 is a plain front schematic view of a particular embodiment of the invention.

Before the present device and method for moving charged particles within a medium are described, it is to be understood that this invention is not limited to the particular component parts of the devices described or process steps of the methods described as such devices and methods may, of course, vary. It is also to be understood that the terminology used herein is for purposes of describing particular embodiments only, and is not intended to be limiting since the scope of the present invention will be limited only by the appended claims.

It must be noted that as used in this specification and the appended claims, the singular forms "a", "an" and "the" include plural referents unless the context clearly dictates otherwise. Thus, for example, reference to "a medium" includes one or more different media mixed together or separated from each other as well as different types of media known to those skilled in the art, reference to "an electrical field" includes a plurality of different electrical fields (of the type described) which may be applied in a number of different ways in order to obtain the effects of the type described herein, and reference to "the process step" includes any number of such steps which will be equivalent to the steps described herein and so forth.

Referring now to the drawings, a specific embodiment of an analytical device useful in carrying out methods of the present invention is shown schematically. The device is on a Card 1 which may be comprised of a number of different types of materials such as various polymeric materials generally referred to as plastics. Further, the Card 1 may be in a variety of different sizes. For convenience, the card could be produced in the size of a conventional credit card.

The Card 1 includes a hollowed-out area or Trench 2 to which, again, may be of any size but for convenience might preferably be produced on the credit card size Card 1 so that the Trench 2 is about 1–10 centimeters in length and has a depth of about 5–25 microns. The cross-sectional shape (not shown) of the Trench 2 may vary and be rectangular, oval, circular or otherwise. It is preferably a flattened oval with the flat surface providing desired optical properties.

The Trench 2 is filled with a medium 3 which may be a buffer solution, polymeric solution, surfactant micellular dispersion or gel of the type generally used in connection with analytical separation techniques. For example, polyacrylamide gel used in PAGE analytical procedures is extremely useful in connection with the present invention. A variety of material may be used along or in combination with other materials which materials should provide frictional resistance to the charged particles and not substantially interfere with the electrical fields.

The Card 1 has plated thereon a plurality of electroplated finger-like electrodes 4–10. Only 7 electrodes are shown on the Card 1 for purposes of simplicity. However, photoelectroplating technology could be utilized to provide hundreds of different electrodes along the length of even a relatively small (1–10 cm) Trench 2.

The electrodes can be spaced apart from each other at any given interval. In connection with this embodiment of the invention, there are preferably 400 to 800 electrodes and they are preferably placed at regular intervals approximately 1-100 microns apart. Some preferred embodiments of the device include 5-25 electrical fields, 50-100 electrical fields, and 500 to over 1000 electrical fields. The electrodes creating these fields may be placed apart from one another at a distance 0.01 to 10 centimeters, but are more preferably placed at a range of about 1-100 microns apart from each other.

The electrodes 4-10 are either simultaneously biased by the application of different voltages to each of the electrodes 4-10 or sequentially biased by the application of different voltages which are biased in a programmed manner. Since the spacing of the electrodes 4-10 is small, it is possible to attain relatively high field strength between the electrodes even while applying relatively low voltages. This is a substantial advantage of the present invention over prior art methods which utilize only one electrical field over the entire medium (having a large dimension) and thus require the application of substantially large voltages.

The electrodes 4-10 are biased or fired simultaneously or sequentially and the magnitude of the field applied across any given electrode or all of the electrodes is adjustable over any given range at any given instant in time. The ability to activate the electrodes in any given fashion and apply different voltages across any given electrode gives rise to a greatly improved ability to separate molecules moving within the medium from each other in an extremely precise fashion, thus obtaining analytical resolution of different types of molecules to a degree far beyond that of conventional techniques.

The Card 1 as well as the Trench 2 and electrode connections 4-10 can be readily and economically produced by standard microelectronic fabrication techniques. Accordingly, multiple copies of nearly identical cards can be readily reproduced with a high degree of accuracy. The fidelity and economy of production are important features of the invention. Since the substrate of the card is preferably a rigid polymeric material such as polymethylmethacrylate, polycarbonate, polyethylene terepthalate, polystyrene or styrene copolymers, the card itself does not have a surface charge. Accordingly, there is no (or negligible) surface charge in the Trench 2, and therefore the problem of electroend-osmosis which is a substantial problem in connection with high performance capillary electrophoresis techniques which utilize glass capillaries which generally must be coated with a polymer in order to suppress the electroend-osmosis. The polymer material can be made substantially non-porous. Accordingly, the charged particles such as proteins are not absorbed and loss of sample during separation is minimal.

It is important to note that the gel-filled channel 2 on the Card 1 does not have to contain cross-linked gels tethered to the wall. This greatly relieves the stress formed during polymerization and cross-linking. The gels need not be tethered to the wall because only a small fraction of the gel 3 in the Trench 2 is under applied electrical field at any given time. Since only a small portion of the gel 3 in the Trench 2 is subjected to the field at a given moment the field does not extrude the gel 3 out of the Trench 2 in any fashion.

The Card 1 having the Trench 2 and electrode connections 4-10 thereon can be produced by a variety of different techniques known to those skilled in the art. In general, one method for producing such a device is as follows. First, a substrate support such as a polymethylmethacrylate card approximately the size of a convention credit card is provided. The surface of the card itself is not electrically conducting nor is the card. On the card is first deposited a thin layer of an electrically conducting material. The coating may be applied by a variety of different techniques known to those skilled in the art and may be comprised of a variety of different types of materials provided they are capable of conducting electricity. The layer is preferably extremely thin on the order of 100 angstroms to a few microns of thickness. The electrically conducting layer is then coated with a layer of material which is both light-sensitive and non-conducting. Once the light-sensitive, non-conducting layer completely covers the electrically conducting layer, a mask is applied to the surface of the light-sensitive, non-conducting layer. After the mask covers the layer, it is exposed to light after which the mask is removed from the light-sensitive, non-conducting layer. Since the light-sensitive layer has been exposed to light at certain portions not covered by the mask, these exposed portions can be removed by conventional technology which renders these portions easily removable. When the exposed areas have been removed, the underlying electrically conductive layer is exposed. These exposed portions will, of course, provide the plurality of electrode connections to the Trench 2.

As will be apparent to those skilled in the art, the mask utilized in the above production procedure can be produced so as to provide hundreds of different electrode connections to the Trench 2. Further, rather than utilizing the photolithographic technique generally described above, it is possible to utilize other techniques such as employing various types of laser technologies and/or other technologies such as silk-screening and vapor deposition which make it possible to provide extremely small (in size) and large numbers of electrodes to the Trench 2. The greater the number of electrodes, the less voltage which needs to be supplied to each electrode and the more accurately it is possible to control the motion of the charged particles within the trench.

Once the card having the electrodes thereon is produced, the Trench 2 must be filled with a medium 3 which is preferably in the form of a polyacrylamide gel material or a buffered solution with or without a synthetic polymer; alone or in combination with a surfactant. After the gel has been added, a sample of material is then placed at one end of the medium and time-dependent and/or variable position-dependent voltages are applied to the electrodes. Although it is possible to supply the voltage to the electrodes in a variety of different manners, it is most preferable to supply the voltage so that electrical fields are sequentially activated one after another in a single direction so as to provide a traveling electrical wave which moves in a single direction along the trench. This wave or waves can be made to move at a variety of speeds depending upon the particular types of molecules being separated. As the wave or waves move, charged particles will be drawn through the medium within the Trench 2. Charged particles which tend to move more quickly will, of course, will be drawn through the medium by moving waves which move quickly along the length of the trench. However, particles which tend to move slowly through the medium 3 can only be moved by waves which move generally slowly through the medium 3.

Although the above-described traveling electrical waves are the preferred method of carrying out the separation processing of the invention, similar separation and resolution capabilities can be obtained in another manner. For example, all of the electrodes positioned along the Trench 2 may be biased simultaneously but have different voltages depending on the electrode spacing and position of any given electrode. The voltages supplied to any given electrode may also be changed continuously over time so as to create different wave-like force affects on the charged particles within the medium and move the particles through the medium at different rates based on factors such as the size, shape and charge of the particles being moved through the medium.

The embodiment described above can be modified in a variety of different fashions. For example, it is possible for the electrodes to have opposing ends on either side of the Trench 2. If the device is constructed in this fashion, charged particles will be moved through the medium 3 in a zig-zag fashion as the different electrodes are activated.

In order to avoid the zig-zag movement of the charged particles through the medium 3, a variety of other embodiments are possible. For example, two cards can be produced wherein one card is substantially the mirror image of the other. The two cards are placed in facing abutment to each other so that the Trench 2 forms an enclosed column. In accordance with this embodiment, the electrode lines do not end at the edge of the Trench 2, but rather continued across the trench on both the top and the bottom. Thus, electrical potential will permeate around the column formed at a plurality of different spaced intervals along the column. By sequentially activating the electrodes, an electrical field wave is caused to move from one end of the column to the other. This creates an effect which draws charged particles through the medium within the column. Again, faster molecules are driven through the medium by moving waves which move quickly along the column and slower molecules will be moved into the medium by waves which move more slowly. By providing a plurality of different speeds of moving waves, it is possible to precisely resolve different bands or groups of charged particles within the medium.

Alternatively, the electrodes on the device may be fired simultaneously in accordance with a predetermined scheme which will create a complex voltage profile across the entire length of the column. The voltage profile will create forces on the charged particles within the column and can be changed over time in order to obtain precise resolution of different species or groups of charged particles within a sample being resolved.

Regardless of the embodiment of the invention which is constructed, it is preferable for the electrodes to be connected to an electronic computer which computer has programmed software dedicated to providing the moving waves or voltage profile along the Trench 2. Various different types of software can be provided so as to obtain the best possible resolution with respect to separating various types of charged particles from one another.

In yet a more sophisticated embodiment of the invention, the computer software which is connected to the electrodes can be made interactive with an optical detection device such as an ultra violet or fluorescence spectrometer. The spectrometer can be focused singly or at various points along the medium 3 in the Trench 2. As the ultra violet spectrometer reads different types of particles being moved to different portions of the medium 3, the information can be sent to the computer which can adjust the speed of the waves or voltage distribution profiles being generated in order to more precisely fine-tune the resolution of the charged particles being moved through the medium 3.

It will apparent to those skilled in the art that the Trench 2 can be in any shape. More specifically, the Trench 2 can be fashioned so that it has a plurality of branches thereon. Each of the branches of the Trench 2, along with the trench itself can be filled with a buffer solution. Thereafter, the base of each of the branches can be supplied with a particular charged reactant material. The charged reactant materials can then be moved into contact with one another by utilizing the moving electrical wave generated by the computer. Accordingly, sophisticated computer programs can be set up in order to provide for synthesis or sequencing protocols of a variety of different types of molecules. For example, different nucleotides can be reacted to form DNA and different amino acids can be reacted to form proteins. These reactions can be carried out at greatly increased speeds as compared with conventional mechanical technologies. In addition to increased speeds, the yield is vastly improved due to the precision with which the reactants can be moved.

In addition to carrying out synthesis reactions in a manner described above, it is possible to carry out DNA or protein sequencing procedures. In connection with these procedures, individual amino acids on proteins or individual nucleotides on DNA molecules can be successively cleaved from one end of the molecule. As the amino acid or nucleotide is cleaved, it can be moved to a given location within the device and identified such as by utilizing a spectrometer. The use of such a sequencing methodology obviates the need for valves, reagents, bottles, washing, filtration and many of the tedious operations which are mechanical in nature and necessary in connection with conventional sequencing methodologies.

In addition to the separation, synthesis and sequencing methods described above, the present invention is useful for a variety of additional purposes. For example, it is possible to utilize specific embodiments of the invention in order to separate impurities from large mixtures of compounds and thus carry out a purification processing which is substantially more refined than vacuum fractionization processing. A mixture of components can be separated into a variety of pure groups and moved along parallel tracks. Upon resolving the mixtures, the desired components can be guided by the electrical wave fields in lateral directions at a given precise moment in time and caused to react with a given neighboring reactant. Alternatively, selected components may be guided to trenches filled with antigen-antibodies reactive with given charged particles being moved in the medium or moved into contact with complimentary components, dyes, fluorescent tags, radio tags, enzyme-specific tags or other types of chemicals for any number of purposes such as various transformations which are either physical or chemical in nature. Further, bacterial or mammalian cells, or viruses may be sorted by complicated trench networks which networks are in connection with a plurality of electrodes capable of generating fields in a variety of different ways in order to move the cells or viruses through the fields based on the size, charge or shape of the particular material being moved. Separated cells or viruses may be analyzed or modified subsequently.

Figure 2:
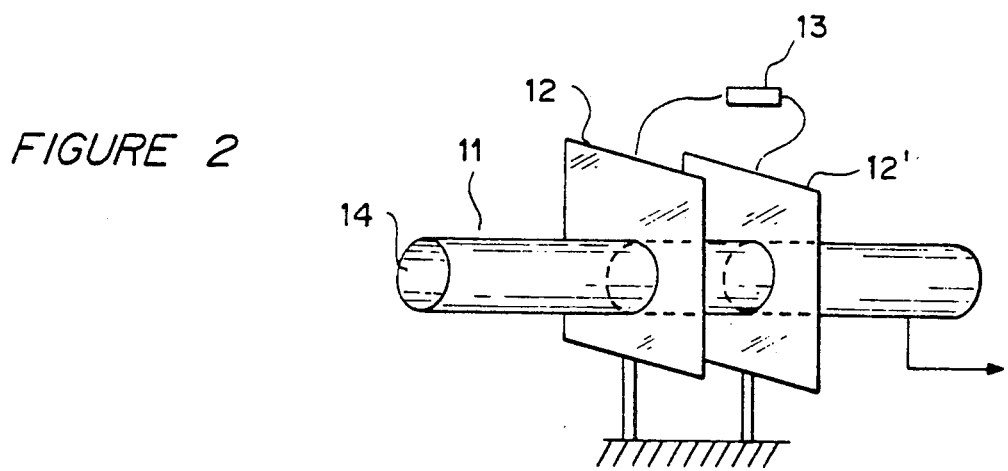
FIG. 2 is a perspective schematic view of a second embodiment of the invention.

The embodiment shown within FIG. 2 is generally utilized for the purification of large quantities of biomacromolecules including proteins and DNA as well as charged molecules, polyelectrolytes, bacteria and viruses. The separation results obtained utilizing this embodiment are based on the different mobilities of charged particles in a given medium when the particles in the medium are subjected to an applied electrical field. In accordance with this embodiment it is not necessary to provide a plurality of electrodes or complex electrical fields. The invention may be carried out utilizing a single pair of electrodes by creating relative motion between the medium holding the sample and the electrodes.

In the embodiment shown within FIG. 2, the cylindrical rod 11 passes through a pair of electrodes 12 and 12' which are connected to a power source 13 for supplying the necessary voltage. In this embodiment the electrodes 12 and 12' are in the form of parallel plates with holes centrally located therein which enables the imposition of an electrical field which creates a force on the charged molecules within a medium 14 inside the cylinder 11. The cylinder 11 and electrodes 12 and 12' are moved relative to each other in a controlled manner. Only the portion of the rod 11 between electrodes 12 and 12' is under the influence of any forces from the electrical field. Accordingly, only charged particles within the medium 14 residing in the particular segment under the influence of the field will be caused to move within the cylinder 11. Since any given sample of materials injected into the medium 14 will exhibit different mobilities within the medium 14 the charged particles in the medium can be separated away. Fast moving charged particles will be able to keep up with a field which is quickly moving by quickly moving the electrodes 12 nd 12' relative to the cylinder 11. Slower moving species of charged particles will fall behind quickly and find themselves within a field-free zone. The voltage 13 supplied to the electrodes 12 and 12' can, of course, be turned on and off as desired. For example, cylinder 11 can be moved in the direction of the arrow through electrodes 12 and 12' until the end of the cylinder 11 is reached. The power can then be turned off and the rod returned to its original position and the process repeated as many times as necessary in order to obtain the desired separation. By varying the speed at which the cylinder 11 and electrodes 12 and 12' are moved, a high degree of separation resolution is possible.

It should be pointed out that the medium such as the medium of 14 present in the cylinder 11 can be in any shape. For example, the medium may be in the form of a rectangular slab of gel and one or more pairs of electrodes creating one or more different kinds of electric fields can be moved relative to the slab in order to create moving electrical fields which will move particles through the gel to obtain precise separation of different types of charged particles in a sample.

It is possible to manually move the cylinder 11 relative to the electrodes 12 and 12' to obtain the separation effect desired. However, it is pointed out that one or more pairs of electrodes can be placed in connection with a mechanical means so that these electrodes can be automatically moved by the mechanical means along the length of the cylinder 11 to obtain separation of charged particles within the medium 14. Alternatively, it is, of course, possible to connect the cylinder 11 to a mechanical means for moving the cylinder 11 relative to the electrodes 12 and 12' in order to obtain the separation effect desired. Simultaneous movement of both the electrodes and the cylinder is, of course, possible. A variety of different types of simple robotics known to those skilled in the art can be utilized to provide such mechanical means for moving either or both the cylinder 11 or electrodes 12 and 12' to obtain the desired results. In addition to being in a variety of different shapes, the medium 14 can be a variety of different types of materials of the type described above in connection with the embodiment shown in FIG. 1 which includes the medium material 3.

While the present invention has been described with reference to specific embodiments, it should be understood by those skilled in the art that obvious changes may be made and equivalents may be substituted without departing from the true spirit and scope of the invention. In addition, many modifications may be made to adapt the methods and devices of the present invention to particular situations, materials, compositions of matter, processes, process step or steps, to the objective, spirit and scope of the present invention. All such modifications are intended to be within the scope of the claims appended hereto.

What is claimed is:

1. A method for moving charged particles through a medium, comprising:
   placing the charged particles in a movement area having defined boundaries, formed on a non-porous, non-electrically conductive substrate with neglible surface charge, and containing multiple electrodes at each end and within each movement area, the electrodes separated by a distance between one and 100 microns, the electrodes providing a plurality of electrical fields to the movement area, and a medium therein, wherein the medium is comprised of particles different from the charged particles and provides frictional resistance to the charged molecules moving through the medium;
   generating a moving electrical field along a given direction of the medium by sequentially activating electrodes placed along the movement area in a time-controlled fashion; and
   continuing to generate the fields in order to cause the charged particles to move in response to the field through the medium.

2. The method as claimed in claim 1, wherein the medium is in the form of a gel.

3. The method as claimed in claim 2, wherein the gel is a cross-linked polyacrylamide gel.

4. The method as claimed in claim 1, wherein the medium is in the form of a liquid.

5. The method as claimed in claim 4, wherein the liquid is a liquid selected from the group consisting of liquid polymer solutions, liquid surfactant micellular solutions, and liquid suspensions containing packed particles having a porous or solid form.

6. A method for moving charged particles through a medium, comprising:
   placing the charged particles in a movement area having defined boundaries, formed on a non-porous, non-electrically conductive substrate with neglible surface charge, and containing multiple electrodes at each end and within each movement area, the electrodes separated by a distance between one and 100 microns, and providing a plurality of electrical fields to the movement area, and a medium therein, wherein the medium is comprised of particles different from the charged particles and provides frictional resistance to the charged molecules moving through the medium;

generating a voltage profile along a given direction of the movement area by simultaneously activating electrodes placed along the movement area with different voltages so as to provide the voltage profile; and continuing to generate the voltage profile in a manner to cause the charged particles to move through the medium in response to the forces created by the voltage profile.

7. A method for reacting particles comprising providing a device for moving charged particles through a medium, comprising a movement area with defined boundaries formed on a non-porous, non-electrically conductive substrate having neglible surface charge;

a medium held in the movement area, the medium comprising material different from the particles to be reacted;

multiple electrodes at each end and within each movement area, the electrodes separated by a distance between one and 100 microns, and providing a plurality of electrical fields to the movement area, the fields being of sufficient strength to move the charged molecules through the medium and from one electrical field to another along the movement area in a controlled manner, placing particles to be reacted into the movement area, and applying a voltage or electrical potential to the electrodes to move the particles to be reacted together under conditions promoting the reaction.

8. The method of claim 7 wherein the particles are degraded.

9. A device for moving charged particles through a medium, comprising:

a movement area with defined boundaries formed on a non-porous, non-electrically conductive substrate having neglible surface charge;

a medium held in the movement area, the medium comprising material different from the charged particles to be moved, the medium providing frictional resistance to the charged molecules to be moved; and multiple electrodes at each end and within each movement area providing a plurality of electrical fields to the movement area, the electrodes separated by a distance between one and 100 microns, the fields being of sufficient strength to move the charged molecules through the medium and from one electrical field to another along the movement area in a controlled manner.

10. The device as claimed in claim 1, wherein the means for providing a plurality of electrical fields provides at least 5 electrical fields.

11. The device as claimed in claim 1, wherein the medium is in the form of a gel.

12. The device as claimed in claim 11, wherein the gel is a cross-linked polyacrylamide gel.

13. The device as claimed in claim 9, wherein the medium is in the form of a liquid.

14. The device as claimed in claim 13, wherein the liquid is a liquid selected from the group consisting of liquid polymer solutions, liquid surfactant micellular solutions, and liquid suspensions containing packed particles having a porous or solid form.

15. The device of claim 1 for moving charged particles through a medium, comprising:

a movement area defined by polymeric material which forms a surface which surface has embedded therein trenches hollowed out into the surface;

a first electrode positioned at a given position on the surface at a given point abutting a trench on the surface; and a second electrode positioned on the surface of the polymeric material which a second electrode is positioned at a distance from the first electrode.

16. The device as claimed in claim 15, wherein the polymeric material is translucent.

17. The device as claimed in claim 15, wherein the polymeric material is transparent and dimensionally rigid.

18. The device of claim 9 wherein the substrate is formed of a material selected from the group consisting of polymethylmethacrylate, polycarbonate, polyethylene terepthalate, polystyrene, and polymer coated glass.

19. The device of claim 9 further comprising sensing devices located adjacent to the movement area.

20. The device of claim 9 further comprising computer means for controlling the voltage applied to the electrodes.

21. The device of claim 9 further comprising reservoirs connected to the movement area.

* * * * *